US011929577B2

(12) United States Patent
Brigham et al.

(10) Patent No.: US 11,929,577 B2
(45) Date of Patent: Mar. 12, 2024

(54) BLOOD PRESSURE MEASUREMENT DEVICE CHARGING CONNECTOR

(71) Applicants: OMRON Corporation, Kyoto (JP); OMRON HEALTHCARE Co., Ltd., Kyoto (JP)

(72) Inventors: Brian Brigham, Kyoto (JP); Takashi Torihama, Kyoto (JP); Takashi Ono, Kyoto (JP); Takanori Nishioka, Kyoto (JP)

(73) Assignees: OMRON CORPORATION, Kyoto (JP); OMRON HEALTHCARE CO., LTD., Kyoto (JP)

(*) Notice: Subject to any disclaimer, the term of this patent is extended or adjusted under 35 U.S.C. 154(b) by 478 days.

(21) Appl. No.: 17/304,502

(22) Filed: Jun. 22, 2021

(65) Prior Publication Data

US 2021/0313740 A1 Oct. 7, 2021

Related U.S. Application Data

(63) Continuation of application No. PCT/JP2019/048030, filed on Dec. 9, 2019.

(30) Foreign Application Priority Data

Dec. 27, 2018 (JP) .................................. 2018-246122

(51) Int. Cl.
*H01R 13/00* (2006.01)
*A61B 5/022* (2006.01)
(Continued)

(52) U.S. Cl.
CPC ....... *H01R 13/631* (2013.01); *A61B 5/02233* (2013.01); *H01R 13/73* (2013.01);
(Continued)

(58) Field of Classification Search
CPC .. H01R 13/631; H01R 13/73; H01R 2201/12; H01R 2201/20; A61B 5/02233; A61B 2560/0214; A61B 2562/227
See application file for complete search history.

(56) References Cited

U.S. PATENT DOCUMENTS 11,832,922 B2 * 12/2023 Iwata ................. A61B 5/02233
2005/0187485 A1 * 8/2005 Fumuro ............. A61B 5/02233
                                                                   600/490

(Continued)

FOREIGN PATENT DOCUMENTS

JP    2003-194972 A    7/2003
JP    2018-196095 A    12/2018
(Continued)

OTHER PUBLICATIONS

International Preliminary Report on Patentability and Written Opinion of the International Searching Authority dated Jul. 8, 2021 in International (PCT) Patent Application No. PCT/JP2019/048030.

*Primary Examiner* — Phuong Chi Thi Nguyen
(74) *Attorney, Agent, or Firm* — Wenderoth, Lind & Ponack, L.L.P.

(57) ABSTRACT

A connector capable of maintaining a state of being connected to a power feeding unit is provided. A blood pressure measurement device charging connector includes a main body including: a first member, a second member facing the first member, the second member including a protrusion including an end surface that makes contact with an inner peripheral surface of a pulling cuff provided on an inner peripheral surface of a curler mounted on the blood pressure measurement device, a rotational shaft configured to rotatably couple the first member and the second member, and a biasing member configured to bias the first member and the second member in an approaching direction; and a connection terminal connected to a power feeding terminal pro- (Continued)

vided in the curler, the connection terminal being provided on the second member side in the first member.

6 Claims, 12 Drawing Sheets

(51) Int. Cl.
*H01R 13/631* (2006.01)
*H01R 13/73* (2006.01)

(52) U.S. Cl.
CPC . *A61B 2560/0214* (2013.01); *A61B 2562/227* (2013.01); *H01R 2201/12* (2013.01); *H01R 2201/20* (2013.01)

(56) References Cited

U.S. PATENT DOCUMENTS

2006/0058687 A1* 3/2006 Kishimoto ......... A61B 5/02233
  600/490
2009/0318779 A1* 12/2009 Tran ................. A61B 5/411
  600/595
2014/0011391 A1* 1/2014 Hung ................ A61B 5/14532
  439/377

FOREIGN PATENT DOCUMENTS

WO    2018/151069 A1    8/2018
WO    2018/179645 A1    10/2018

* cited by examiner

[Fig. 1]
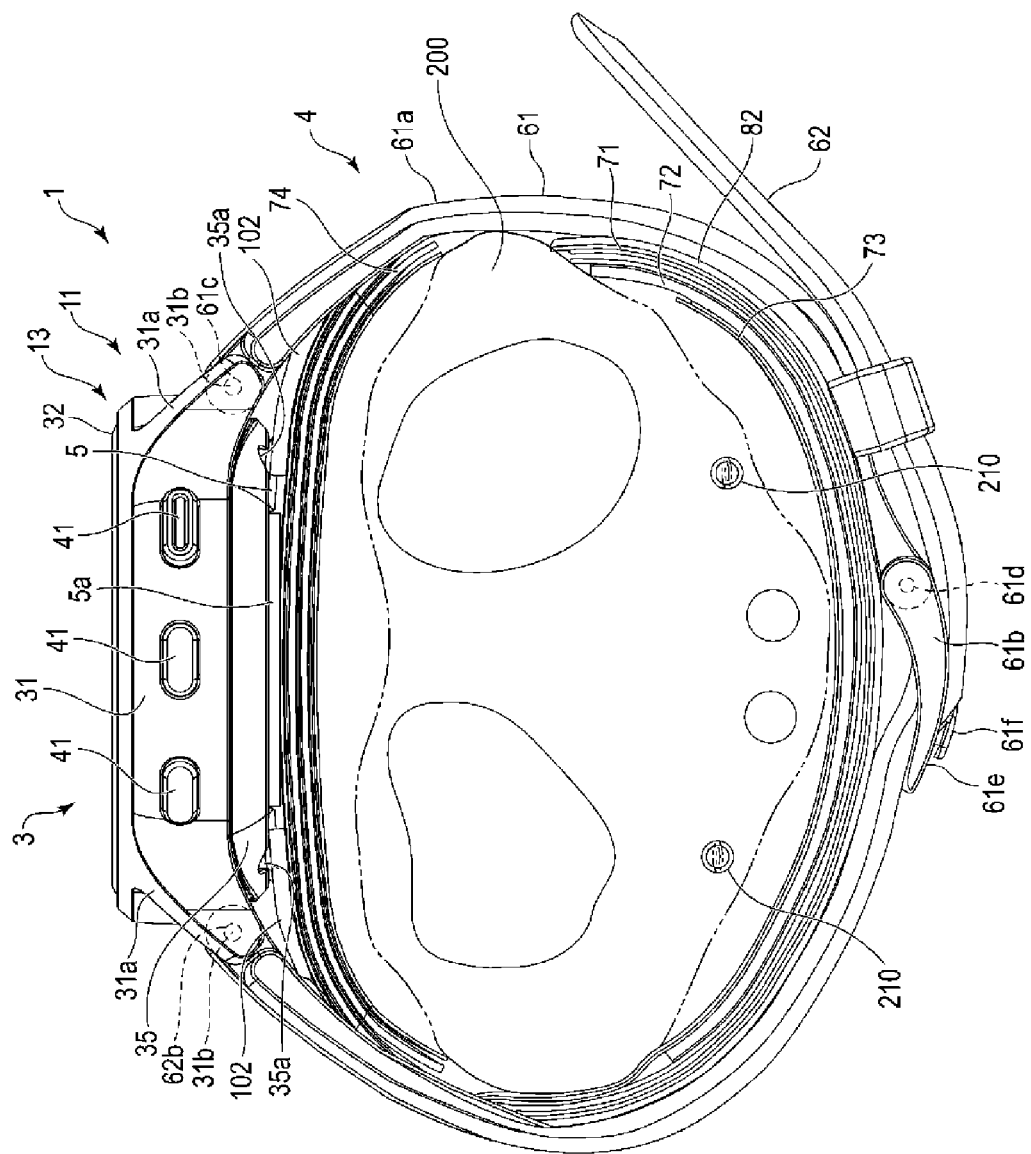

[Fig. 2]
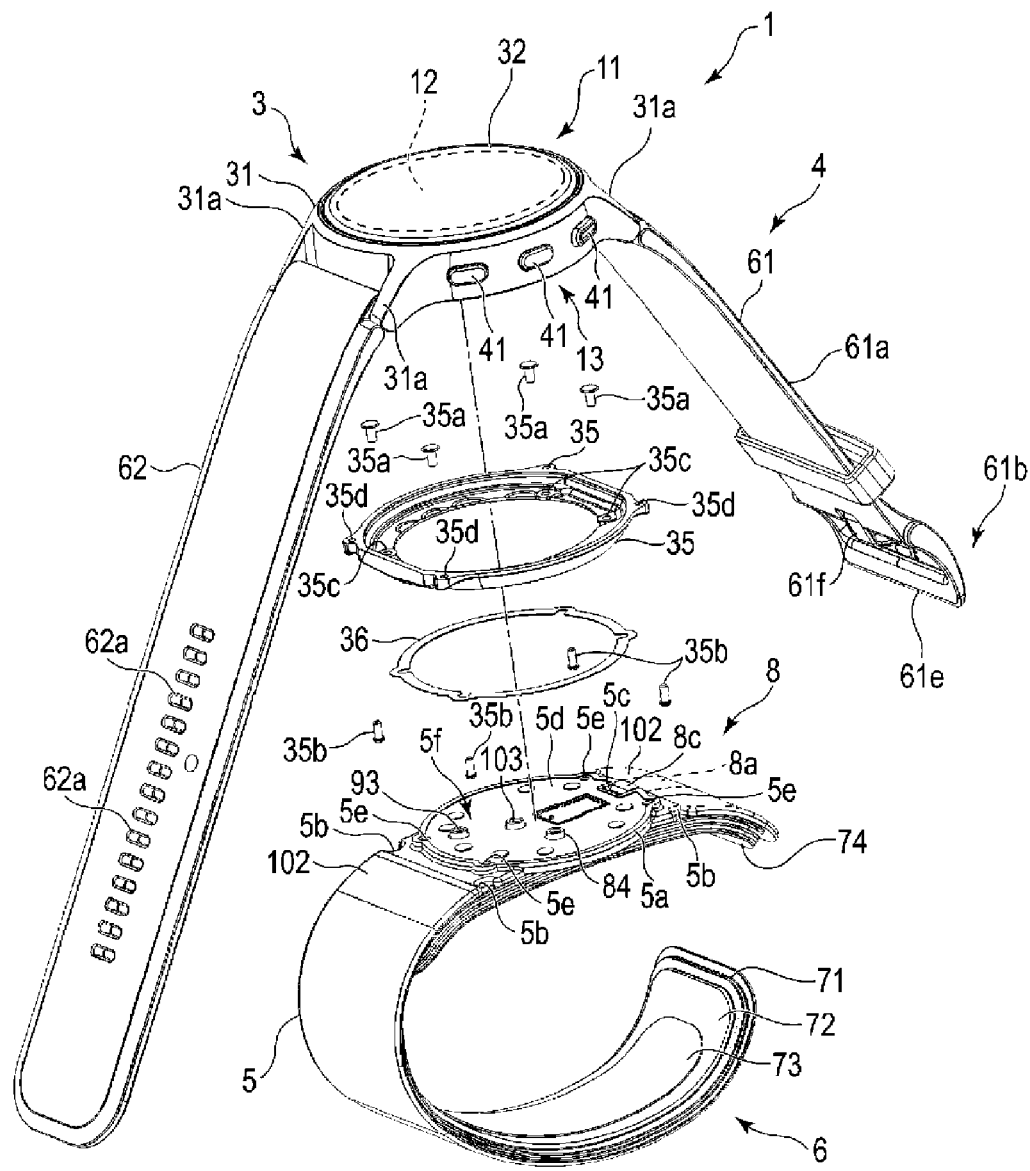

[Fig. 3]
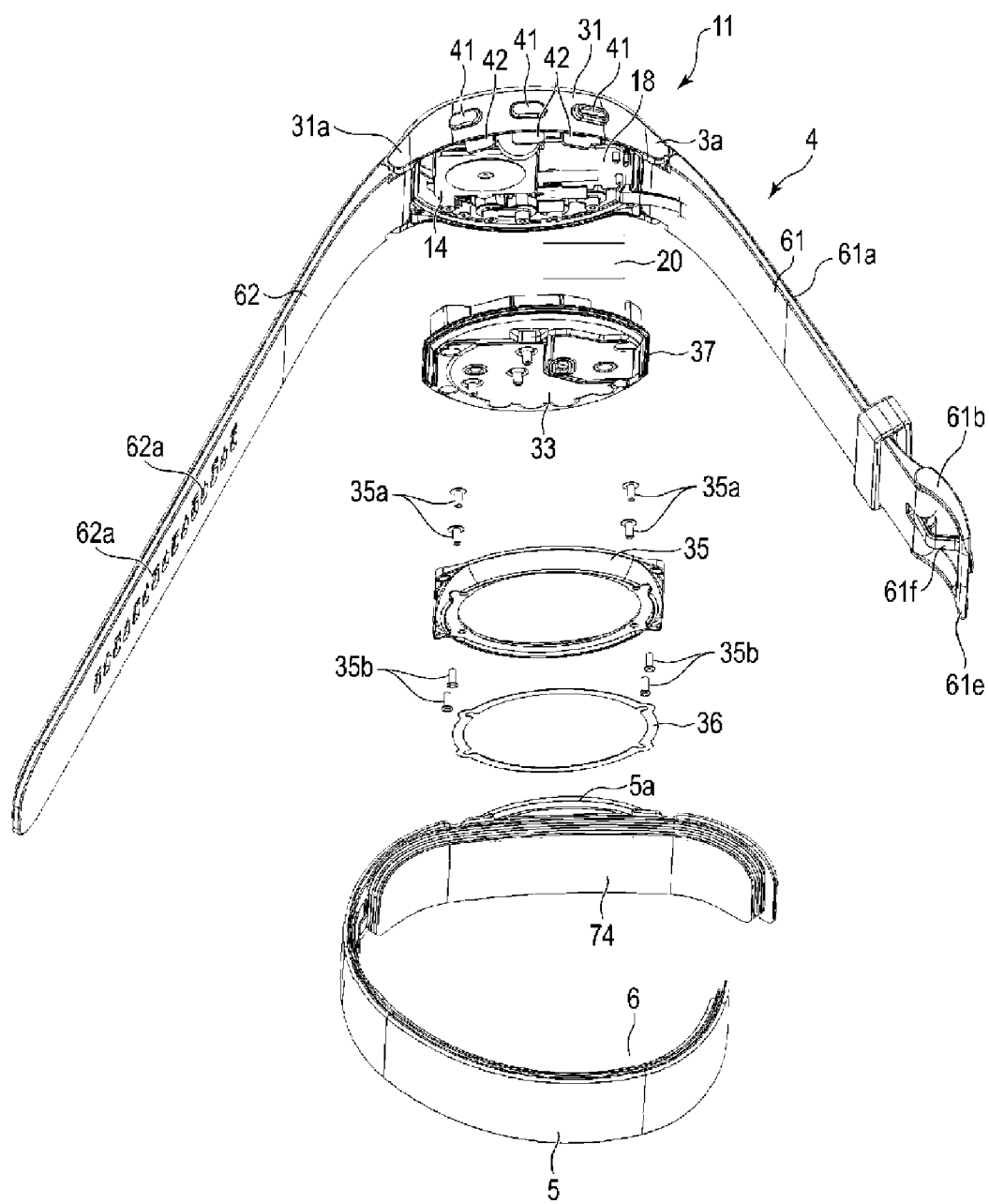

[Fig. 4]
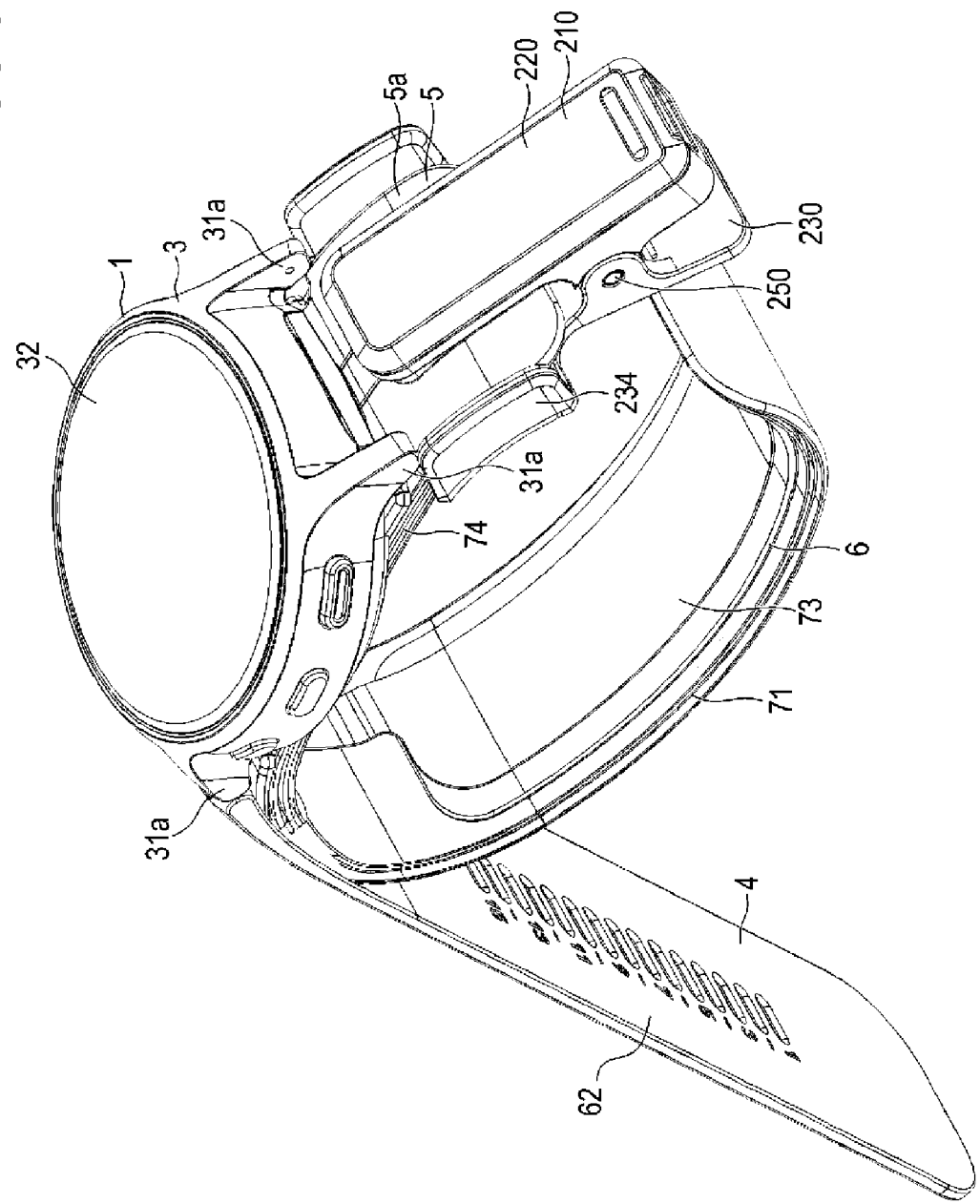

[Fig. 5]
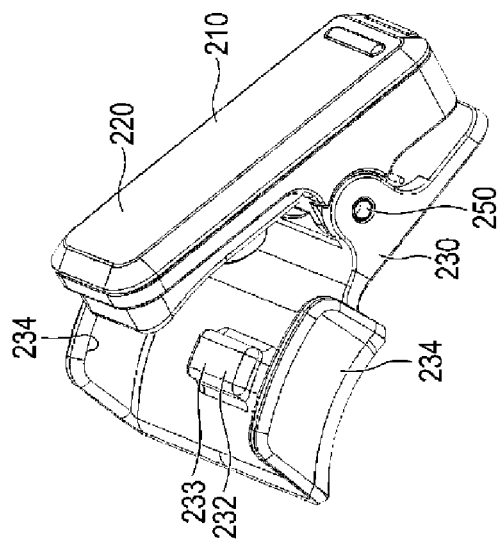
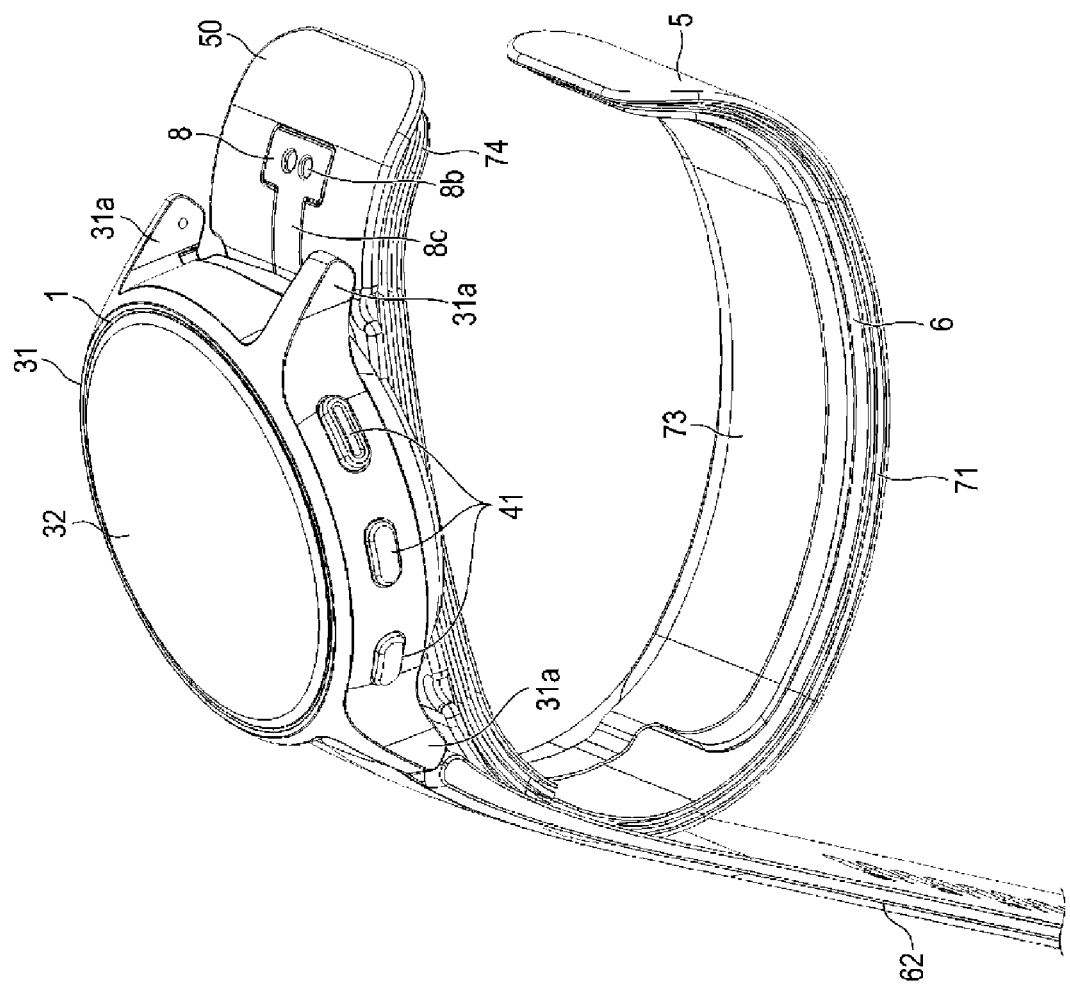

[Fig. 6]
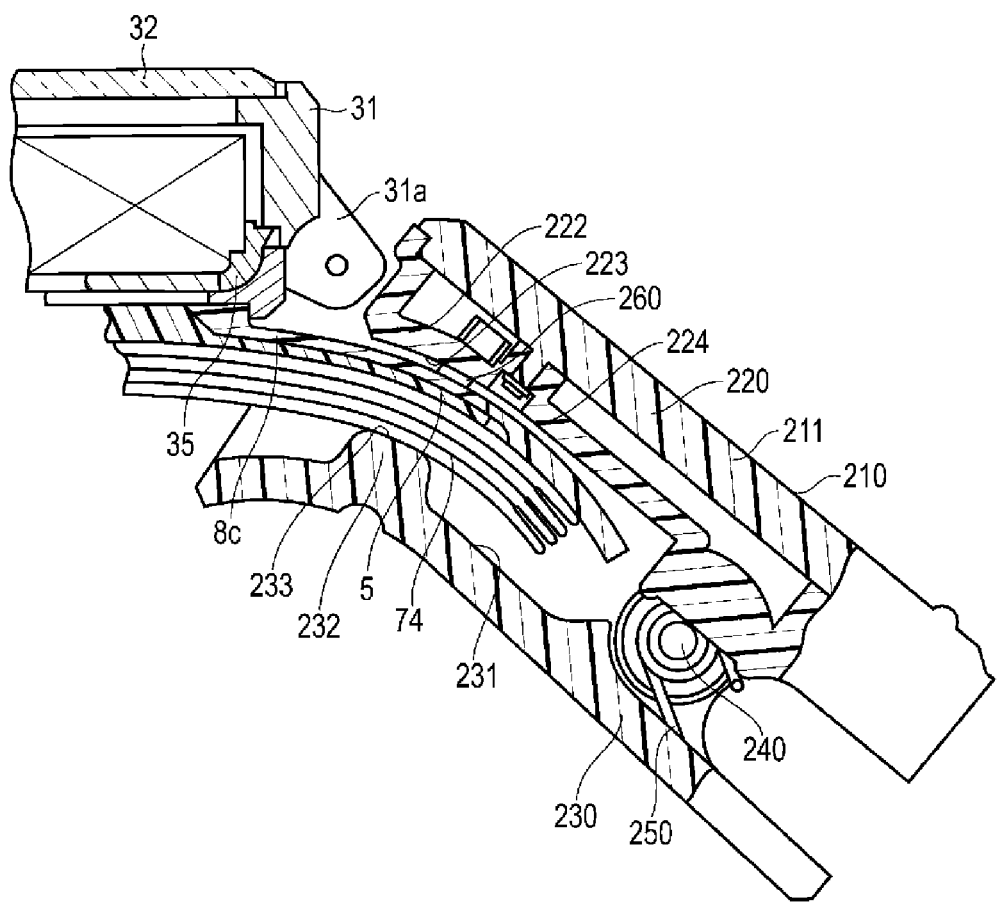

[Fig. 7]
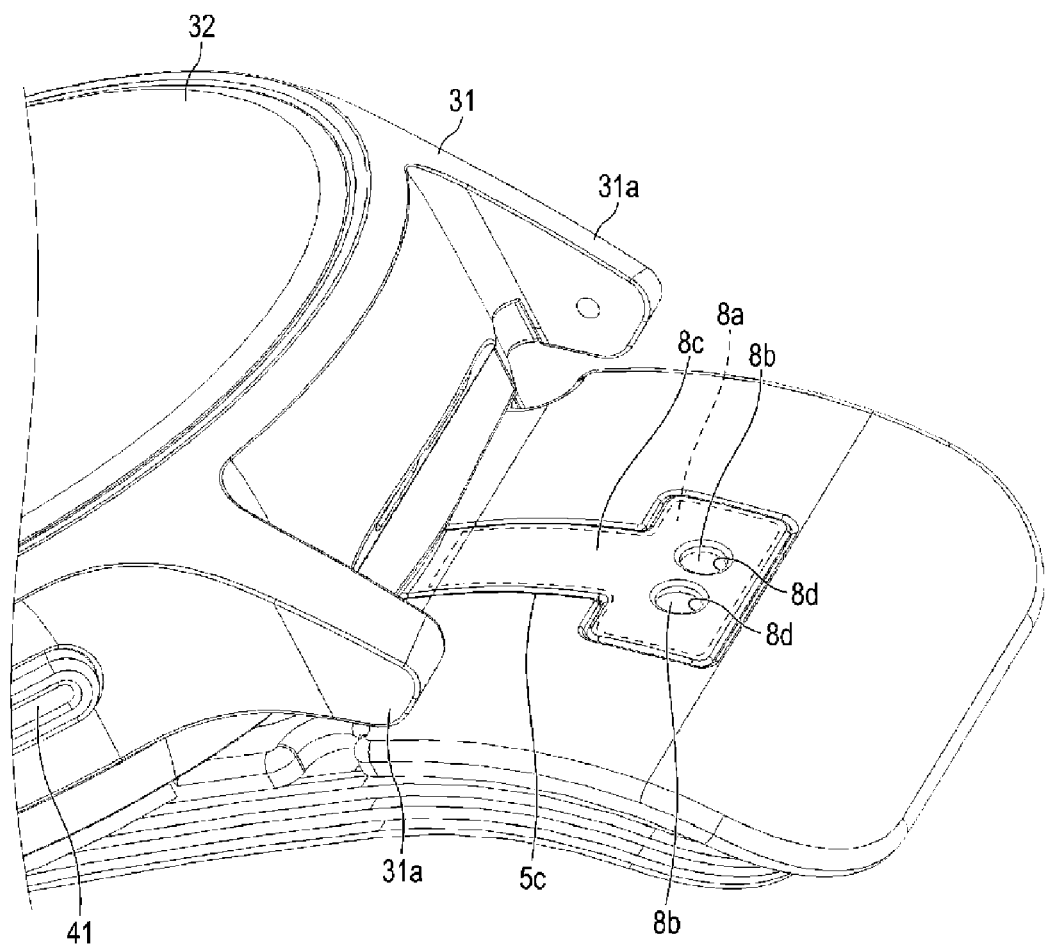

[Fig. 8]
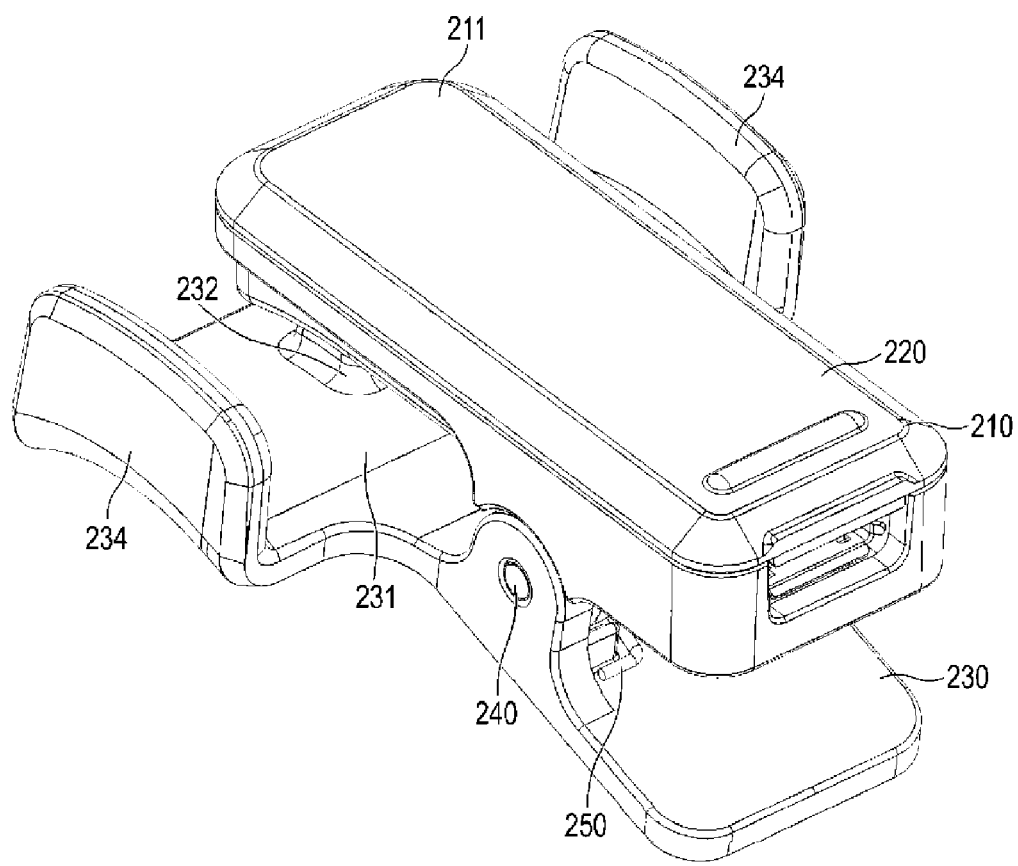

[Fig. 9]
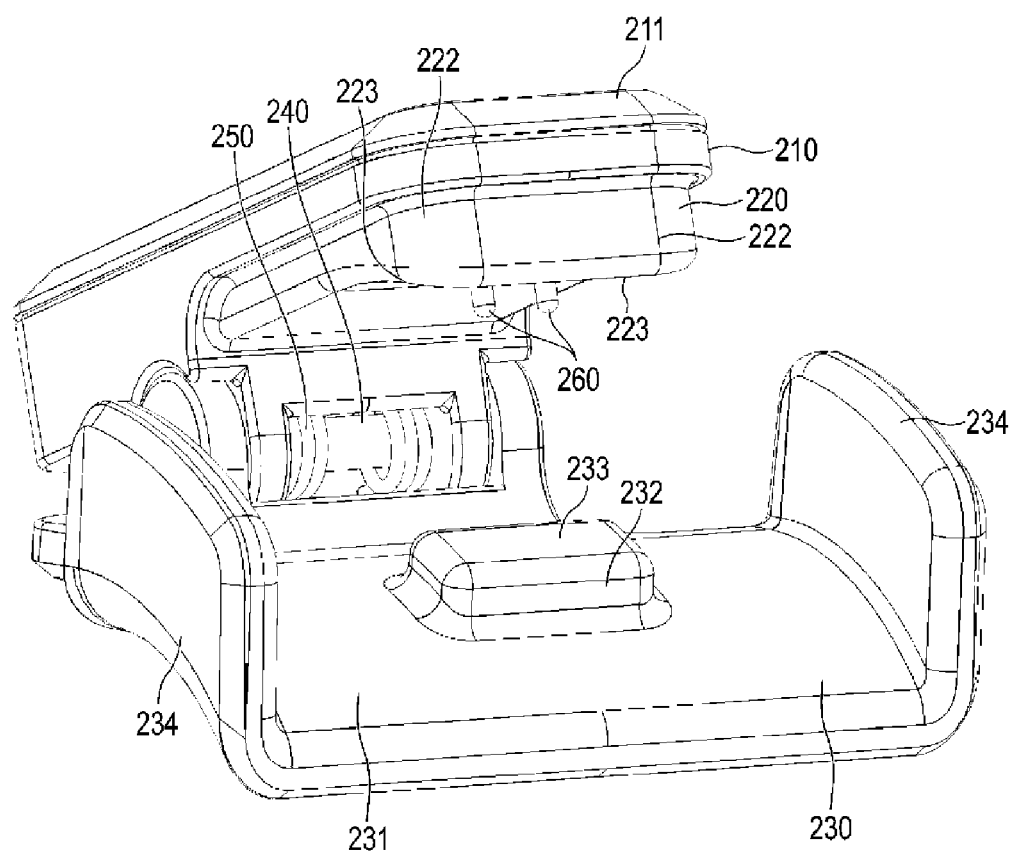

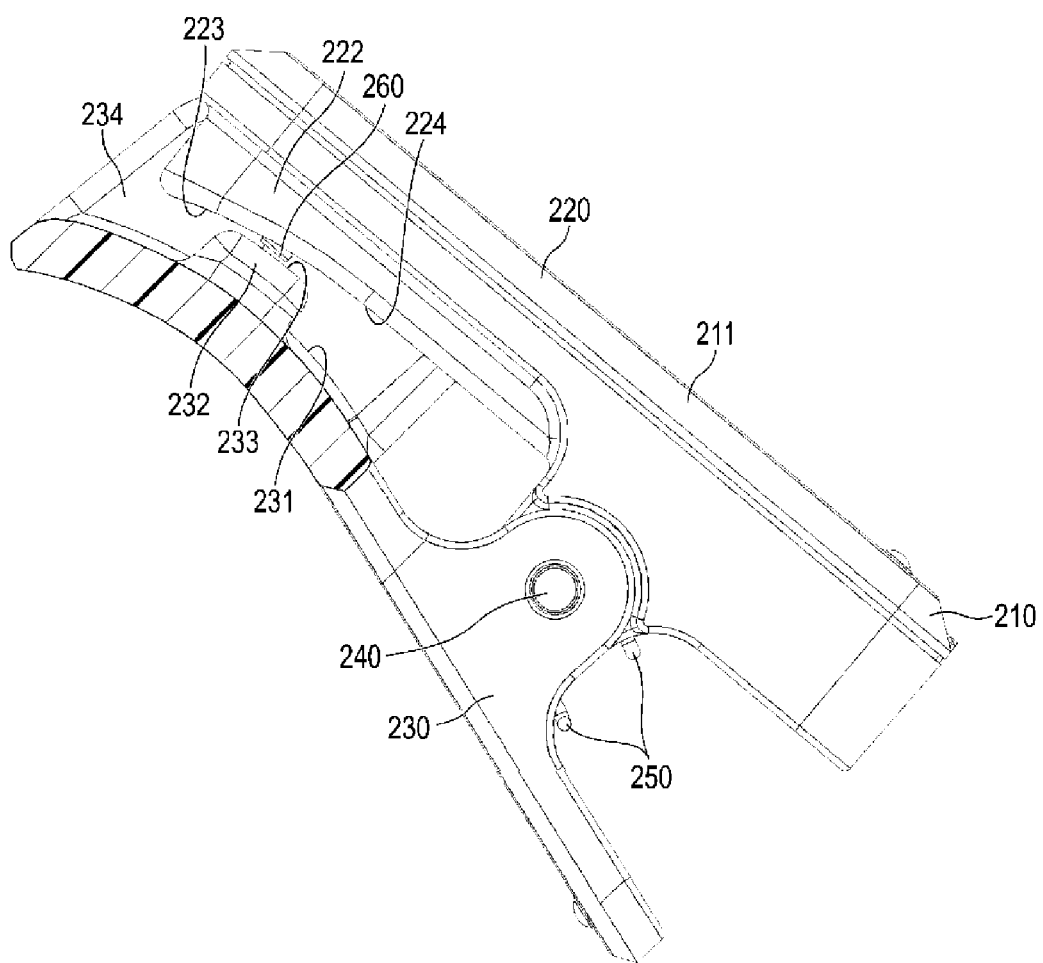
[Fig. 10]

[Fig. 11]
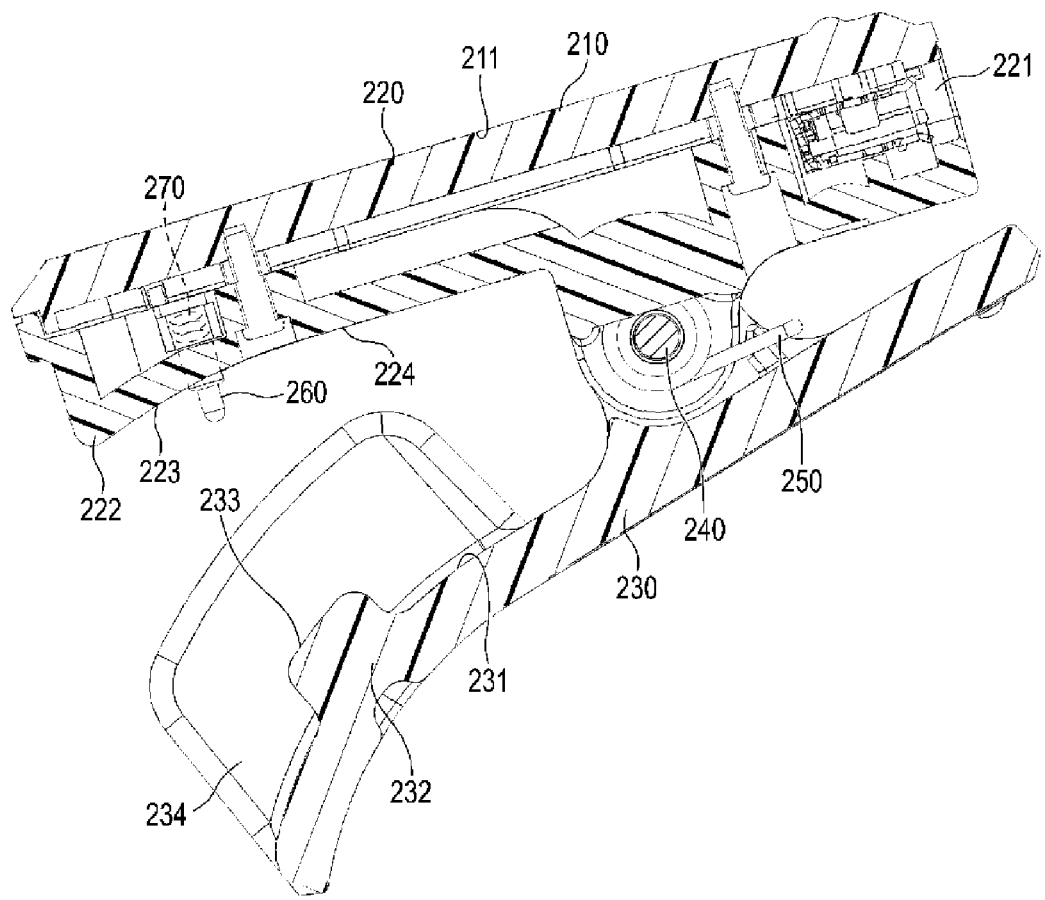

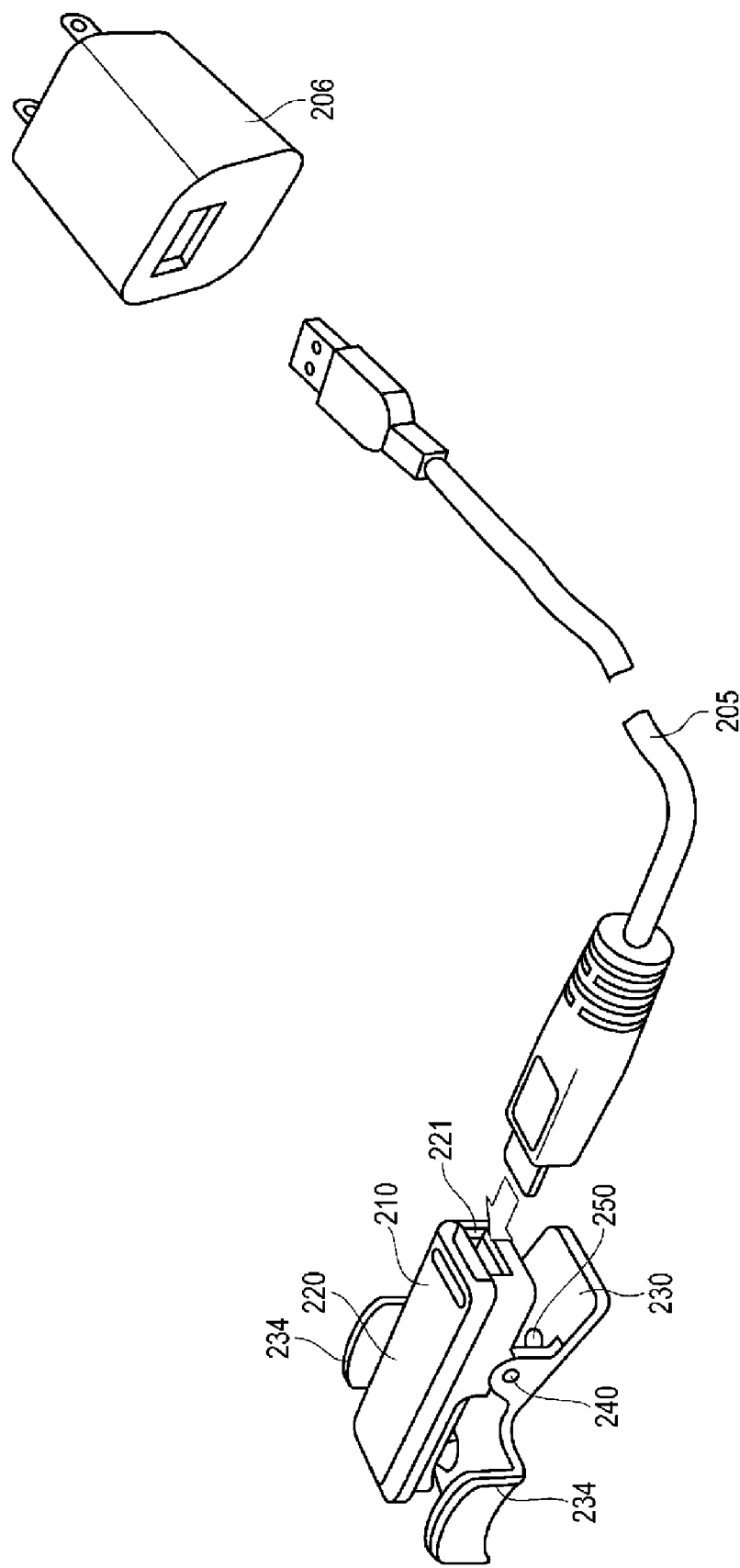
[Fig. 12]

BLOOD PRESSURE MEASUREMENT DEVICE CHARGING CONNECTOR

CROSS-REFERENCE TO RELATED APPLICATIONS

This application is the U.S. national stage application filed pursuant to 35 U.S.C. 365(c) and 120 as a continuation of International Patent Application No. PCT/JP2019/048030, filed Dec. 9, 2019, which application claims priority to Japan Patent Application No. 2018-246122, filed Dec. 27, 2018, which applications are incorporated herein by reference in their entireties.

TECHNICAL FIELD

The present invention relates to a connector used for charging a blood pressure measurement device for measuring blood pressure.

BACKGROUND ART

Blood pressure measurement devices used to measure blood pressure are used not only in medical facilities, but also in the home as a means of checking health status.

For example, in a blood pressure measurement device, a cuff is wrapped around the upper arm or wrist of a living body, the cuff is inflated and deflated, and the pressure sensor detects the pressure of the cuff to measure blood pressure by detecting the vibration of the arterial wall.

A blood pressure measurement device generally called an integrated type is known in which the cuff and the device main body that supplies fluid to the cuff are integrally configured, for example. The blood pressure measurement device of the integrated type uses, for example, a secondary battery as a means of supplying power to the device main body.

For a device that is fixed to a living body, such as the above-described blood pressure measurement device, a configuration is known in which a power feeding unit to which a connector for charging a secondary battery is connected is placed on a belt that is fixed to a living body, such as a wrist, as disclosed in JP 2003-194972 A (see, for example, PTL1).

In the blood pressure measurement device, the cuff is required to be in intimate contact with the wrist when inflated. Therefore, a configuration is known in which a curler is used to bring the inflated cuff into intimate contact with the wrist.

CITATION LIST

Patent Literature

PTL1: JP 2003-194972 A

SUMMARY OF INVENTION

Technical Problem

In a blood pressure measurement device equipped with a curler as described above, a power feeding unit may be disposed in the curler. However, since the curler is configured in a shape curved to fit the circumference of the wrist, the posture of the connector that is electrically connected to the power feeding unit tends to be unstable, and as a result, it is difficult to maintain the electrical connection between the charging unit and the power feeding unit.

In view of this, an object of the present invention is to provide a blood pressure measurement device charging connector that can maintain a state of being connected to a power feeding unit.

Solution to Problem

An aspect provides a blood pressure measurement device charging connector connected to a blood pressure measurement device attached to a wrist, the blood pressure measurement device charging connector including a clip including a first member, a second member facing the first member, the second member including a protrusion including an end surface that makes contact with an inner peripheral surface of a cuff provided on an inner peripheral surface of a curler mounted on the blood pressure measurement device, the curler being curved to follow a circumferential direction of the wrist with one end and another end spaced from each other, a rotational shaft configured to rotatably couple the first member and the second member, and a biasing member configured to bias the first member and the second member in an approaching direction, and a terminal connected to a power feeding terminal provided in the curler, the terminal being provided on the second member side in the first member.

According to this aspect, the inner peripheral surface of the cuff is supported using the protrusion, thereby the connector can be stably held at the curler. Thus, the state where the connection terminal is connected to the power feeding terminal can be maintained.

In the blood pressure measurement device charging connector according to the aspect, the end surface of the protrusion is configured as a flat surface extending in a tangential direction at a contact portion of a contact surface of the cuff, or a curved surface along the contact portion.

According to this aspect, the end surface of the protrusion is configured as a flat surface extending in a tangential direction at a contact portion of a contact surface on an inner peripheral surface of the cuff, or a curved surface along the contact portion. Thus, the protrusion makes surface contact with the cuff, or makes contact with it in a wide range, and thus the connector can be stably held at the curler.

In the blood pressure measurement device charging connector according to the aspect, the terminal and the protrusion face each other in a rotational direction of the first member and the second member.

According to this aspect, generation of a rotation moment at the cuff and the curler sandwiched between the connection terminal and the protrusion can be suppressed. Thus, the connector can be stably held at the curler.

In the blood pressure measurement device charging connector according to the aspect, a side opposite to the rotational shaft across a center of the first member on a surface of the first member on the second member side is configured as a curved surface along a facing outer peripheral surface of the curler when the terminal is electrically connected to the power feeding terminal.

According to this aspect, the first protrusion is brought into contact with the outer surface of the curler, thereby the interference of the rotational shaft side of the connector with the curler when the connector is mounted to curler can be suppressed. Further, with the end surface in surface contact with the outer surface of the cover and the curler, the connector can be stably held at the curler.

In the blood pressure measurement device charging connector according to the aspect, the second member includes a wall part configured to restrict a movement of the curler in a width direction.

According to this aspect, with the second member including the wall part, the movement of the curler with respect to the connector in the width direction of the curler can be regulated. Thus, the connection terminal can be guided to the power feeding terminal by only moving the connector to the case side.

In the blood pressure measurement device charging connector according to the aspect, a spring provided in the first member and configured to bias the terminal to the second member side is further provided, and the power feeding terminal is disposed in a dent of the curler.

According to this aspect, when the connection terminal enters the dent, a click feeling can be generated. With this click feeling, the user can recognize that the connection terminal and the power feeding terminal are connected.

Advantageous Effects of Invention

According to the present invention, it is possible to provide a blood pressure measurement device charging connector that can maintain a state of being connected to a power feeding unit.

BRIEF DESCRIPTION OF DRAWINGS

FIG. 1 is a side view illustrating a blood pressure measurement device according to an embodiment of the present invention.

FIG. 2 is an exploded perspective view illustrating a configuration of the blood pressure measurement device.

FIG. 3 is an exploded perspective view illustrating the configuration of the blood pressure measurement device.

FIG. 4 is a perspective view illustrating the configuration of the blood pressure measurement device and a configuration of a connector.

FIG. 5 is a perspective view illustrating a state where the blood pressure measurement device and the connector are separated from each other.

FIG. 6 is a sectional view illustrating the configurations of the blood pressure measurement device and the connector.

FIG. 7 is a perspective view illustrating a configuration of a curler of the blood pressure measurement device.

FIG. 8 is a perspective view illustrating the configuration of the connector.

FIG. 9 is a perspective view illustrating the configuration of the connector.

FIG. 10 is a sectional view illustrating the configuration of the connector.

FIG. 11 is a partially cutout sectional view illustrating the configuration of the connector.

FIG. 12 is a perspective view illustrating the configuration of the connector and a configuration of a charging cable.

DESCRIPTION OF EMBODIMENTS

An example of a blood pressure measurement device 1 according to an embodiment of the present invention will be described below with reference to FIG. 1 to FIG. 12.

FIG. 1 is a side view illustrating the blood pressure measurement device 1. FIG. 2 is an exploded perspective view illustrating a configuration of the blood pressure measurement device 1. FIG. 3 is a perspective view illustrating the configuration of the blood pressure measurement device 1 as viewed from an angle different from that of FIG. 2. FIG. 4 is a perspective view illustrating the configuration of the blood pressure measurement device 1 and a configuration of a blood pressure measurement device charging connector 210 in the state where the blood pressure measurement device charging connector 210 is connected to a power feeding unit 8. FIG. 5 is a perspective view illustrating a state where the blood pressure measurement device 1 and the blood pressure measurement device charging connector 210 are separated from each other.

FIG. 6 is a sectional view illustrating the configurations of the blood pressure measurement device 1 and the blood pressure measurement device charging connector 210 in the state where the blood pressure measurement device charging connector 210 is connected to the power feeding unit 8. FIG. 7 is a perspective view illustrating a configuration of a curler 5 of the blood pressure measurement device 1, or more specifically, the power feeding unit 8 provided in the curler 5 and the vicinity thereof.

FIG. 8 is a perspective view illustrating the configuration of the blood pressure measurement device charging connector 210. FIG. 9 is a perspective view illustrating the configuration of the blood pressure measurement device charging connector 210 as viewed from an angle different from that of FIG. 8. FIG. 10 is a sectional view illustrating the configuration of the blood pressure measurement device charging connector 210. FIG. 11 is a partially cutout side view illustrating the configuration of the blood pressure measurement device charging connector 210. FIG. 12 is a perspective view illustrating the configuration of the blood pressure measurement device charging connector 210 and a configuration of a charging cable 205.

The blood pressure measurement device 1 is an electronic blood pressure measurement device that is worn on a living body. In the present embodiment, descriptions will be made using an electronic blood pressure measurement device having a configuration of a wearable device that is worn on a wrist 200 of a living body. The blood pressure measurement device 1 is configured to supply power to a power supply unit 18 using the charging cable 205 and the blood pressure measurement device charging connector 210.

As illustrated in FIG. 1 to FIG. 5, the blood pressure measurement device 1 includes a device main body 3, a belt 4 that fixes the device main body 3 to the wrist, the curler 5 disposed between the belt 4 and the wrist, a cuff structure 6 including a pressing cuff 71, a sensing cuff 73 and a pulling cuff 74, and the power feeding unit 8 provided in the curler 5.

The device main body 3 includes, for example, a case 11, a display unit 12, an operation unit 13, a pump 14, the power supply unit 18, and a control substrate 20. The device main body 3 supplies fluid to the cuff structure 6 using the pump 14 and other components.

The case 11 includes an outer case 31, a windshield 32 that covers an opening of the outer case 31 on the side (outer side) opposite to the wrist 200 side, a base 33 provided on the wrist 200 side inside the outer case 31, and a rear cover 35 that covers the wrist 200 side of the outer case 31.

The outer case 31 is formed in a cylindrical shape. The outer case 31 includes pairs of lugs 31a provided at circumferentially symmetric positions on the outer peripheral surface, and spring rods 31b provided between the respective pairs of lugs 31a. The windshield 32 is, for example, a circular glass plate.

The rear cover 35 has an annular configuration that opens on the center side. The rear cover 35 covers the outer peripheral edge side of the end portion of the outer case 31 on the wrist 200 side. When the rear cover 35 is integrally combined with the curler 5, the center opening is covered with the curler 5, and thus the rear cover 35, together with the curler 5, constitutes a rear lid that covers the end portion of the outer case 31 on the wrist 200 side. To be more specific, the rear cover 35 is fixed to the curler 5 with four first fastening members 35a, and is fixed to the end portion of the outer case 31 on the wrist 200 side with four second fastening members 35b. The rear cover 35 includes four hole parts 35c into which the first fastening members 35a to be fixed to the curler 5 are inserted, and four hole parts 35d into which the second fastening members 35b to be fixed to the outer case 31 are inserted. The four hole parts 35c are provided in the bottom portion of the rear cover 35. The four hole parts 35d are provided in four radially outwardly protruded portions in the outer periphery part of the rear cover 35.

The display unit 12 is disposed above the base 33 of the outer case 31 and immediately below the windshield 32. The display unit 12 is electrically connected to the control substrate 20. The display unit 12 is, for example, a liquid crystal display or an organic electroluminescence display. The display unit 12 displays various information such as date and time, and measurement results of blood pressure values such as a systolic blood pressure and a diastolic blood pressure, and heart rates.

The operation unit 13 is configured to allow input of commands from the user. For example, as illustrated in FIG. 1 to FIG. 3, the operation unit 13 includes a plurality of buttons 41 provided in the case 11, a sensor 42 that detects operations of the buttons 41, and a touch panel provided in the display unit 12 or the windshield 32. When operated by the user, the operation unit 13 converts commands into electric signals. The sensor 42 and the touch panel are electrically connected to the control substrate 20, and output electric signals to the control substrate 20.

For example, three buttons 41 are provided. The buttons 41, which are supported by the base 33, protrude from the outer peripheral surface of the outer case 31. The plurality of buttons 41 and a plurality of the sensors 42 are supported by the base 33. The touch panel is provided integrally with the windshield 32, for example.

The pump 14 is, for example, a piezoelectric pump. The pump 14 compresses air, and supplies the compressed air to the cuff structure 6 through a channel that is partially formed in the base. The pump 14 is electrically connected to the control substrate 20.

As illustrated in FIG. 1 to FIG. 4, the belt 4 includes a first belt 61 provided to the pair of lugs 31a and the spring rod 31b on one side, and a second belt 62 provided to the pair of lugs 31a and the spring rod 31b on the other side. The belt 4 is wound around the wrist 200 with the curler 5 therebetween.

The first belt 61 is generally called a parent, and is configured in a belt shape that can be coupled with the second belt 62. As illustrated in FIG. 1 to FIG. 3, the first belt 61 includes a belt part 61a and a buckle 61b. The belt part 61a is configured in a belt shape. The belt part 61a is formed from an elastically-deformable resin material. In addition, the belt part 61a includes therein a sheet-like insert member that is flexible and suppresses the expansion and contraction of the belt part 61a in the longitudinal direction. The belt part 61a includes a first hole part 61c that is formed at one end portion and is orthogonal to the longitudinal direction of the belt part 61a and a second hole part 61d that is formed at the other end portion and is orthogonal to the longitudinal direction of the first belt 61.

The first hole part 61c is provided at an end portion of the belt part 61a. The first hole part 61c has an internal diameter with which the spring rod 31b can be inserted and the first belt 61 can rotate around the spring rod 31b. That is, with the first hole part 61c disposed at the spring rod 31b between the pair of lugs 31a, the first belt 61 is rotatably held by the outer case 31.

As illustrated in FIG. 1 and FIG. 3, the second hole part 61d is provided at the front end of the belt part 61a. The buckle 61b is attached at the second hole part 61d.

As illustrated in FIG. 1 and FIG. 3, the buckle 61b includes a frame member 61e having a rectangular frame shape, and a buckle tongue 61f that is rotatably attached to the frame member 61e. One side of the frame member 61e where the buckle tongue 61f is attached is inserted into the second hole part 61d, and thus the frame member 61e is attached such that it is rotatable with respect to the belt part 61a.

The second belt 62 is generally called a pointed end, and is configured in a belt shape with a width that can be inserted in the frame member 61e. The second belt 62 is formed from an elastically-deformable resin material. In addition, the second belt 62 includes therein a sheet-like insert member that is flexible and suppresses the expansion and contraction of the second belt 62 in the longitudinal direction.

In addition, as illustrated in FIG. 1 and FIG. 2, the second belt 62 includes a plurality of small holes 62a into which the buckle tongue 61f is inserted. In addition, the second belt 62 includes a third hole part 62b that is provided at one end portion and is orthogonal to the longitudinal direction of the second belt 62. The third hole part 62b has an internal diameter with which the spring rod 31b can be inserted and the second belt 62 can rotate around the spring rod 31b. That is, with the third hole part 62b disposed at the spring rod 31b between the pair of lugs 31a, the second belt 62 is rotatably held by the outer case 31.

When the second belt 62 is inserted into the frame member 61e and the buckle tongue 61f is inserted into the small hole 62a, the first belt 61 and the second belt 62 are connected together, and the belt 4 has an annular form following the circumferential direction of the wrist 200 together with the outer case 31. When the belt 4 is in an annular form following the circumferential direction of the wrist 200, the belt 4 presses the curler 5 such that the curler 5 elastically deforms to follow the circumferential direction of the wrist of the wearer of the blood pressure measurement device 1.

As illustrated in FIG. 1 to FIG. 5, the curler 5 is configured in a belt shape that is curved to follow the circumferential direction of the wrist 200. The curler 5 is formed such that one end and the other end are spaced from each other. In the curler 5, the outer surface on one end side is fixed to the rear cover 35 of the device main body 3, for example. One end and the other end of the curler 5 are disposed at a position protruded to one lateral side of the wrist 200 relative to the rear cover 35. In this manner, when the blood pressure measurement device 1 is worn on the wrist 200, one end and the other end of the curler 5 are disposed on the lateral side of the wrist 200. In addition, in the curler 5, one end and the other end are adjacent to each other with a predetermined distance therebetween. The curler 5 is formed from a resin material, for example. As a specific example, the curler 5 is formed from polypropylene with a thickness of approximately 1 mm.

As a specific example, the curler 5 is configured in a belt shape that curves to follow the circumferential direction of the wrist. In addition, the curler 5 includes an annular plate-shaped cover part 5a provided at a position on one end side facing the back hand of the wrist 200, and an escape part 5b provided around the cover part 5a. The cover part 5a constitutes a rear lid together with the rear cover 35. The escape part 5b allows movement of the first fastening member 35a that fixes the rear cover 35 and the outer case 31. The cover part 5a and the adjacent portion of the curler 5 are formed in a plate-shape, and the portions on one end side and the other end side of the cover part 5a are curved in a predetermined curvature, for example. In the curler 5, the length from the cover part 5a to one end is smaller than the length from the cover part 5a to the other end. As a specific example, in the curler 5, the short side from the cover part 5a to one end is disposed on the back hand side of the wrist, and the long side from the cover part 5a to the other end extends from the back hand side of the wrist 200 to the palm side of the wrist through one side of the wrist.

In addition, as illustrated in FIG. 2, the curler 5 is formed in a shape in which the other end is located on the inner peripheral surface side of one end side when one end and the other end are close to each other. As a specific example, the width of the curler 5 in the width direction of the wrist 200 is greater on the back hand side of the wrist 200 than on the palm side of the wrist 200. In the curler 5, the curvature radius of one end on the back hand side of the wrist 200 is greater than the curvature radius of the other end on the palm side of the wrist 200. With this configuration, when the both ends of the curler 5 make contact with each other, the other end is disposed on the inner side of the curler 5 in comparison with one end. In addition, in the curler 5, a dent 5c adjacent to the cover part 5a is provided in a part of the cover part 5a and the outer surface from the cover part 5a to one end side, and more specifically, the outer surface of the short side extending from the cover part 5a.

The curler 5 is fixed to the outer case 31 such that one end and the other end face the second belt 62 of the belt 4. In addition, the curler 5 is curved along the circumferential direction on the palm side of the wrist 200 at least at the position facing the palm side of the wrist 200, and thus holds the cuff structure 6 that faces the palm side of the wrist 200 in the state where the cuff structure 6 is curved to follow the shape of the palm side of the wrist 200.

In addition, the curler 5 has a hardness with flexibility and shape retainability. Here, the flexibility means that the shape deforms in the radial direction when the external force of the belt 4 is applied to the curler 5. For example, the flexibility means that the shape deforms in the lateral view such that it comes closer to the wrist, or it comes along the shape of the wrist, or, it follows the shape of the wrist, when the curler is pressed by the belt 4. In addition, the shape retainability means that the curler 5 can maintain a preformed shape when no external force is applied thereto. For example, the shape retainability of the present embodiment means that the shape of the curler 5 curved along the circumferential direction of the wrist can be maintained.

In the curler 5, the power feeding unit 8 is provided in the curved outer surface. As a specific example, in the outer surface on one end side, the curler 5 includes the dent 5c where the power feeding unit 8 is provided. The dent 5c is formed from below the rear cover 35 to one end. The dent 5c is configured to have a depth with which the power feeding unit 8 provided therein does not protrude from the outer surface of the curler 5, or in other words, a depth with which the power feeding unit 8 is located on the inner surface side below the outer surface of the curler 5.

In the curler 5, the cuff structure 6 is disposed on the inner peripheral surface, and thus the curler 5 holds the cuff structure 6 along the shape of the inner peripheral surface of the curler 5. As a specific example, in the curler 5, the pressing cuff 71 and the pulling cuff 74 are disposed on the inner peripheral surface, and the cuff structure 6 is fixed with a bonding layer provided between the curler 5 and the pressing cuff 71 and the pulling cuff 74, and thus, the curler 5 holds the cuff structure 6. In the present embodiment, the bonding layer is an adhesive agent or a double-sided tape.

As illustrated in FIGS. 1, 2, and 4, the cuff structure 6 includes the pressing cuff 71, a back plate 72, the sensing cuff 73, and the pulling cuff 74. In addition, the cuff structure 6 includes the bonding layer for bonding between the components, and between the curler 5 and the cuffs 71 and 74. The cuff structure 6 is fixed to the curler 5. In the cuff structure 6, the pressing cuff 71, the back plate 72 and the sensing cuff 73 are stacked and disposed on the curler 5, and the pulling cuff 74 is disposed on the curler 5 with a space from the pressing cuff 71, the back plate 72 and the sensing cuff 73.

As a specific example, in the cuff structure 6, the pressing cuff 71, the back plate 72 and the sensing cuff 73 are stacked and fixed in this order in the direction from the inner peripheral surface of the curler 5 to the wrist 200 side, on the inner peripheral surface of the curler 5 on the palm side of the wrist 200. In addition, in the cuff structure 6, the pulling cuff 74 is disposed on the inner peripheral surface of the curler 5 on the back hand side of the wrist 200. Each member of the cuff structure 6 is fixed to the member adjacent thereto in the stacking direction with the bonding layer.

As illustrated in FIG. 5 and FIG. 7, the power feeding unit 8 includes a wiring part 8a, a power feeding terminal 8b, and a cover 8c that covers the wiring part 8a disposed in the dent 5c of the curler 5. One end of the wiring part 8a is connected to the power feeding terminal 8b, and the other end of the wiring part 8a is connected to the control substrate 20. The power feeding terminal 8b is composed of two circular terminals, for example. For example, the wiring part 8a and the power feeding terminal 8b are composed of flexible printed circuits (FPCs) in which a conductive metal film and the like are provided in a base film made of polyimide and the like.

The cover 8c is formed in the same shape as the dent 5c, and covers the dent 5c. The top surface of the cover 8c is flush with the outer surface of the curler 5 on the short side when the cover 8c is provided in the dent 5c. The cover 8c includes a hole 8d through which the power feeding terminal 8b is exposed. The power feeding terminal 8b is disposed at a position of a predetermined depth from the edge of the hole 8d in the hole 8d.

The blood pressure measurement device charging connector 210 includes a main body 211 having a clip shape, and a connection terminal 260 provided in the main body 211 and configured to be connected to the power feeding terminal 8b, for example. As illustrated in FIG. 12, the charging cable 205 is detachably connected to the blood pressure measurement device charging connector 210. The charging cable 205 is a connector with USB connectors provided at both ends, for example. One end of the charging cable 205 is detachably connected to the blood pressure measurement device charging connector 210. The other end of the charging cable 205 is detachably connected to an AC charger 206. The AC charger 206 is connected to a household outlet.

The main body 211 includes a first member 220, a second member 230 facing the first member 220, a rotational shaft 240 that rotatably couples the first member 220 and the second member 230, and a biasing member 250.

The first member 220 is configured in a rectangular plate shape that is long in one direction, for example. As illustrated in FIG. 12, for example, a USB connector 221 to which the charging cable 205 is detachably connected is provided at one end portion of the first member 220.

A surface 223 of another end portion 222 of the first member 220 on the second member 230 side faces a region between the outer case 31 and the power feeding unit 8 in the outer surface of the cover 8c and the curler 5 in the state where the connection terminal 260 is in contact with the power feeding terminal 8b of the power feeding unit 8. The surface 223 is configured as a curved surface along the facing region. Here, "along" means that the surface is configured to be parallel to or approximately parallel to the surface of the facing region.

As illustrated in FIG. 4 and FIG. 5, the second member 230 is configured in a plate shape that is wider than the width of the curler 5 in the width direction of the curler 5. In the second member 230, a protrusion 232 is formed on a surface 231 on the first member 220 side at a position that faces the connection terminal 260.

The protrusion 232 is disposed at a center in the width direction of the curler 5 in the second member 230. An end surface 233 of the protrusion 232 makes contact with the inner peripheral surface of the pulling cuff 74 in the state where the connection terminal 260 is in contact with the power feeding terminal 8b. Further, the end surface 233 is configured as a flat surface extending in the tangential direction at the contact portion where the end surface 233 makes contact with the inner peripheral surface of the pulling cuff 74, or in a curved surface along the contact portion.

It is to be noted that the end surface 233 of the protrusion 232 is configured as a flat surface extending in the tangential direction at the contact portion where the end surface 233 makes contact with the inner peripheral surface of the pulling cuff 74 when charging is performed, or in a curved surface along the contact portion.

In the blood pressure measurement device 1 of the present embodiment, as an example, the power supply unit 18 is charged in the state where the blood pressure measurement device 1 is detached from the user and the pulling cuff 74 is not inflated. The end surface 233 of the protrusion 232 makes contact with the inner peripheral surface of the pulling cuff 74 in an uninflated state. Thus, the end surface 233 of the protrusion 232 is configured as a flat surface extending in the tangential direction at the contact portion where the end surface 233 makes contact with the inner peripheral surface of the pulling cuff 74 in an uninflated state, or in a curved surface along the contact portion.

In addition, the second member 230 includes guide wall parts 234 at both ends in the width direction of the curler 5. Each guide wall part 234 protrudes to the first member 220 side. The width between the two guide wall parts 234 is greater than the width of the curler 5 and can regulate the movement of the blood pressure measurement device charging connector 210 in the width direction with respect to the curler 5. The outer surface of the guide wall part 234 is configured as a curved surface. The curved outer surface of the guide wall part 234 is configured as a curved surface that is easy for users to hold with their fingers.

The rotational shaft 240 rotatably couples the USB connector 221 side of the first member 220 and the side of the second member 230 opposite to the protrusion 232.

The length to the rotational shaft 240 from one end on the opposite side with respect to the rotational shaft 240 of the second member 230 is sufficiently large so that the front end of the curler 5 does not make contact with the rotational shaft 240 even in the state where the connection terminal 260 is connected to the power feeding terminal 8b of the power feeding unit 8.

The biasing member 250 is configured to bias one end side of the first member 220 on the side opposite to the USB connector 221 and the protrusion 232 side of the second member 230, in the approaching direction. It is to be noted that both of one end of the first member 220 on the side opposite to the USB connector 221 and one end of the second member 230 on the protrusion 232 side are on the outer case 31 side in the state where the blood pressure measurement device charging connector 210 is fixed to the curler 5. The biasing member 250 is a torsion spring provided at the rotational shaft 240 with one end supported by the first member 220 and the other end supported by the second member 230, for example.

The connection terminals 260 are provided in the same number as the power feeding terminals 8b and are electrically connected to the power feeding terminals 8b. The connection terminal 260 is electrically connected to the charging cable 205 in the first member 220.

The connection terminal 260 is configured in a columnar shape, e.g., a cylindrical shape. The connection terminal 260 is supported by a biasing member 270 in the first member 220, and is protruded from a surface 224 on the second member 230 side. The surface 224 includes the surface 223. The connection terminal 260 protrudes from the surface 224 toward the second member 230 side.

The biasing member 270 biases the connection terminal 260 in the direction in which the connection terminal 260 is protruded from the surface 224. The biasing member 270 is, for example, a spring. When the connection terminal 260 is pressed and the biasing member 270 is compressed, the protruding amount of the connection terminal 260 with respect to the surface 223 of the first member 220 decreases. In other words, the connection terminal 260 is supported by the biasing member 270 such that it can move forward and backward with respect to the surface 224, and is biased to the second member 230 side.

The connection terminal 260 is disposed at a position facing the protrusion 232 in the rotational direction of the first member 220 and the second member 230. To be more specific, in the present embodiment, the distance from the center of the rotational shaft 240 to the axis of the connection terminal 260 is the same as the distance from the center of the rotational shaft 240 to the center of the end surface 233 of the protrusion 232.

Next, an example of a method of connecting the blood pressure measurement device charging connector 210 to the power feeding unit 8 will be described. In the state where the blood pressure measurement device charging connector 210 is detached from the wrist 200 and each of the pulling cuff 74, the sensing cuff 73 and the pressing cuff 71 is uninflated, the user presses the USB connector 221 side of the first member 220 and the second member 230 in the approaching direction so as to separate the end portions of the first member 220 and the second member 230 on the connection terminal 260 side.

Next, the user exposes the power feeding unit 8 provided in the curler 5 by peeling off the first belt 61.

Next, the user brings, into contact with the outer peripheral surface of the curler at the front end side that is more distal than the power feeding unit 8, the distal end of the connection terminal 260 and the surface 223 of the end portion on the side opposite to the USB connector 221 of the first member 220. At this time, the biasing member 270 is compressed, and the protruding amount of the connection terminal 260 from the surface 224 of the first member 220 is smaller than that of the initial position.

Next, the user moves the blood pressure measurement device charging connector 210 to the case 11 side with the surface 223 in contact with the outer peripheral surface of the curler 5.

When the blood pressure measurement device charging connector 210 is moved to the case 11 side by a predetermined distance, the curler 5 and the pulling cuff 74 are housed between the two guide wall parts 234 of the second member 230. When a part of the curler 5 is housed between the two guide wall parts 234, the movement of the blood pressure measurement device charging connector 210 with respect to the curler 5 in the width direction of the curler 5 is restricted. With this restriction, the connection terminal 260 and the power feeding terminal 8b face each other in the direction in which the blood pressure measurement device charging connector 210 is moved.

When the blood pressure measurement device charging connector 210 is further moved to the case 11 side, the distal end portion of the connection terminal 260 enters the hole 8d of the cover 8c. When the distal end portion of the connection terminal 260 enters the hole 8d, the connection terminal 260 makes contact with the power feeding terminal 8b. In addition, when the distal end of the connection terminal 260 enters the hole 8d, a click feeling is generated.

With the click feeling, the user recognizes that the connection terminal 260 is connected to the power feeding terminal 8b. When receiving the click feeling, the user stops the movement of the blood pressure measurement device charging connector 210, and releases the pressure on the end portions of the first member 220 and the second member 230.

When the pressure on the first member 220 and the second member 230 is released, the biasing member 250 moves the second member 230 to the pulling cuff 74 side. When the second member 230 is moved to the pulling cuff 74 side, the end surface 233 of the protrusion 232 makes contact with the inner peripheral surface of the pulling cuff 74.

As described above, in the blood pressure measurement device 1 according to the present embodiment, the inner peripheral surface of the pulling cuff 74 is supported by the protrusion 232, and thus the blood pressure measurement device charging connector 210 can be stably held at the curler 5. Thus, the state where the connection terminal 260 is connected to the power feeding terminal 8b can be maintained.

Further, the end surface 233 of the protrusion 232 is configured as a flat surface extending in the tangential direction at the contact portion where the end surface 233 makes contact with the inner peripheral surface of the pulling cuff 74, or the curved surface along the contact portion where the end surface 233 makes contact with the inner peripheral surface of the pulling cuff 74. Thus, the protrusion 232 makes surface contact with the pulling cuff 74, or makes contact with the pulling cuff 74 in a wide range, and therefore the blood pressure measurement device charging connector 210 can be stably held at the curler 5.

Further, the connection terminal 260 and the protrusion 232 face each other in the rotational direction of the first member 220 and the second member 230. Thus, generation of a rotation moment at the pulling cuff 74 and the curler 5 sandwiched between the connection terminal 260 and the protrusion 232 can be suppressed. Thus, the blood pressure measurement device charging connector 210 can be stably held at the curler 5.

Further, the distance from the center of the rotational shaft 240 to the axis of the connection terminal 260, and the distance from the center of the rotational shaft 240 to the center of the protrusion 232 are set as the same distance, and thus the connection terminal 260 faces the center of the protrusion 232 in the rotational direction of the first member 220 and the second member 230. Thus, the generation of a rotation moment at the pulling cuff 74 and the curler 5 sandwiched between the connection terminal 260 and the protrusion 232 can be further suppressed. Thus, the blood pressure measurement device charging connector 210 can be stably held at the curler 5.

Further, one end of the first member 220 on the outer case 31 side protrudes to the second member 230 side, and further, the surface 223 on the second member 230 side of the end portion of the first member 220 on the outer case 31 side is configured in a shape along the outer surface of the curler 5 and the cover 8c that the surface 223 faces when the connection terminal 260 and the power feeding terminal 8b are connected. In this manner, one end of the first member 220 on the outer case 31 side is brought into contact with the outer surface of the curler 5, so that it is possible to suppress the interference of the rotational shaft 240 side of the blood pressure measurement device charging connector 210 with the curler 5 when the blood pressure measurement device charging connector 210 is mounted to the curler 5. Further, with the surface 223 configured as a curved surface along the facing region of the outer surface of the curler 5 and the cover 8c, the blood pressure measurement device charging connector 210 can be stably held at the curler 5.

Further, since the second member 230 includes the guide wall part 234, the movement of the curler 5 with respect to the blood pressure measurement device charging connector 210 in the width direction of the curler 5 can be regulated. Thus, the connection terminal 260 can be guided to the dent where the power feeding terminal 8b is housed by only moving the blood pressure measurement device charging connector 210 to the case 11 side.

Further, with the connection terminal 260 supported by the biasing member 270, a click feeling can be generated when the connection terminal 260 enters the hole 8d. With this click feeling, the user can recognize that the connection terminal 260 and the power feeding terminal 8b are connected.

Further, the length from one end of the second member 230 on the outer case 31 side to the rotational shaft 240 is sufficiently large so that it does not make contact with the rotational shaft 240 even in the state where the curler 5 and the pulling cuff 74 are disposed between the first member 220 and the second member 230, and the connection terminal 260 is connected to the power feeding terminal 8b. Thus, in a process of attaching the blood pressure measurement device charging connector 210 to the power feeding unit 8, the curler 5 does not interfere with the blood pressure measurement device charging connector 210. Thus, the blood pressure measurement device charging connector 210 can be smoothly attached to the power feeding terminal 8b.

Note that the present invention is not limited to the embodiments described above, various embodiments and modifications within the spirit of invention are possible. Furthermore, each of the embodiments may be combined as appropriate to obtain the combined effects of the embodiments. Moreover, the embodiments described above include various stages of invention, and various inventions may be obtained by appropriately combining the multiple configuration requirements disclosed.

REFERENCE SIGNS LIST

1 Blood pressure measurement device
3 Device main body
4 Belt
5 Curler
5a Cover part
5b Escape part
5c Dent
5e Screw hole
6 Cuff structure
8 Power feeding unit
11 Case
12 Display unit
13 Operation unit
14 Pump
18 Power supply unit
20 Control substrate
31 Outer case
31a Lug
31b Spring rod
32 Windshield
33 Base
35 Rear cover
35a First fastening member
35b Second fastening member
35c Hole part
35d Hole part
41 Button
42 Sensor
61 First belt
61a Belt part
61b Buckle
61c First hole part
61d Second hole part
61e Frame member
61f Buckle tongue
62 Second belt
62a Small hole
62b Third hole part
71 Pressing cuff
73 Sensing cuff
74 Pulling cuff (Cuff)
200 Wrist
205 Charging cable
206 AC charger
210 Blood pressure measurement device charging connector
211 Main body
220 First member
221 USB connector
230 Second member
231 Surface
232 Protrusion
233 End surface
234 Guide wall part
240 Rotational shaft
250 Biasing member
260 Connection terminal
270 Biasing member

The invention claimed is:

1. A blood pressure measurement device charging connector connected to a blood pressure measurement device attached to a wrist, the blood pressure measurement device charging connector comprising:
a clip including:
a first member,
a second member facing the first member, the second member including a protrusion including an end surface that makes contact with an inner peripheral surface of a cuff provided on an inner peripheral surface of a curler mounted on the blood pressure measurement device, the curler being curved to follow a circumferential direction of the wrist with one end and another end spaced from each other,
a rotational shaft configured to rotatably couple the first member and the second member, and
a biasing member configured to bias the first member and the second member in an approaching direction; and
a terminal connected to a power feeding terminal provided in the curler, the terminal being provided on the second member side in the first member.

2. The blood pressure measurement device charging connector according to claim 1, wherein the end surface of the protrusion is configured as a flat surface extending in a tangential direction at a contact portion of a contact surface of the cuff, or a curved surface along the contact portion.

3. The blood pressure measurement device charging connector according to claim 1, wherein the terminal and the protrusion face each other in a rotational direction of the first member and the second member.

4. The blood pressure measurement device charging connector according to claim 1, wherein a side opposite to the rotational shaft across a center of the first member on a surface of the first member on the second member side is configured as a curved surface along a facing outer peripheral surface of the curler when the terminal is electrically connected to the power feeding terminal.

5. The blood pressure measurement device charging connector according to claim 1, wherein the second member includes a wall part configured to restrict a movement of the curler in a width direction.

6. The blood pressure measurement device charging connector according to claim 1, further comprising a spring provided in the first member and configured to bias the terminal to the second member side,
wherein the power feeding terminal is disposed in a dent of the curler.

* * * * *